US011583198B2

(12) United States Patent
Genicot et al.

(10) Patent No.: US 11,583,198 B2
(45) Date of Patent: Feb. 21, 2023

(54) COMPUTER-IMPLEMENTED METHOD AND SYSTEM FOR CONTACT PHOTOPLETHYSMOGRAPHY (PPG)

(71) Applicant: QOMPIUM, Hasselt (BE)

(72) Inventors: Matthieu Genicot, Leuven (BE); Amaury Vanvinckenroye, Braives (BE); Kobe Leysen, Bilzen (BE); Lars Grieten, Zutendaal (BE); Jo Van Der Auwera, Meerhout (BE); Bieke Van Gorp, Kasterlee (BE)

(73) Assignee: QOMPIUM, Hasselt (BE)

( * ) Notice: Subject to any disclaimer, the term of this patent is extended or adjusted under 35 U.S.C. 154(b) by 424 days.

(21) Appl. No.: 16/640,221

(22) PCT Filed: Aug. 10, 2018

(86) PCT No.: PCT/EP2018/071728
§ 371 (c)(1),
(2) Date: Feb. 19, 2020

(87) PCT Pub. No.: WO2019/042739
PCT Pub. Date: Mar. 7, 2019

(65) Prior Publication Data
US 2020/0359922 A1    Nov. 19, 2020

(30) Foreign Application Priority Data

Aug. 30, 2017 (EP) .................................. 17188626

(51) Int. Cl.
*A61B 5/024* (2006.01)
*A61B 5/0245* (2006.01)
(Continued)

(52) U.S. Cl.
CPC ........ *A61B 5/02416* (2013.01); *A61B 5/0245* (2013.01); *A61B 5/02427* (2013.01);
(Continued)

(58) Field of Classification Search
None
See application file for complete search history.

(56) References Cited

U.S. PATENT DOCUMENTS

2009/0203998 A1 * 8/2009 Klinghult ........... A63B 24/0003
600/443
2009/0326349 A1 * 12/2009 McGonigle ........ A61B 5/02416
600/323
(Continued)

FOREIGN PATENT DOCUMENTS

CN        106357879 A    1/2017
EP        3207862 A1     8/2017
(Continued)

OTHER PUBLICATIONS

Karlen et al., "Detection of the Optimal Region of Interest for Camera Oximetry," 35th Annual International Conference of the IEEE EMBS, Jul. 2013, pp. 2263-2266.
(Continued)

*Primary Examiner* — Kennedy Schaetzle
(74) *Attorney, Agent, or Firm* — Workman Nydegger

(57) ABSTRACT

A computer-implemented method for contact photoplethysmography, abbreviated contact PPG, comprises obtaining during a time interval plural PPG signals for sub-regions of a lens or video frame; and combining the plural PPG signals to thereby obtain a multi-region PPG signal.

17 Claims, 10 Drawing Sheets

(51) Int. Cl.
*A61B 5/00* (2006.01)
*A61B 5/361* (2021.01)

(52) U.S. Cl.
CPC .............. *A61B 5/361* (2021.01); *A61B 5/726* (2013.01); *A61B 5/7221* (2013.01); *A61B 5/7264* (2013.01); *A61B 5/7275* (2013.01); *A61B 2562/0233* (2013.01)

(56) References Cited

U.S. PATENT DOCUMENTS

| | | | |
|---|---|---|---|
| 2011/0004069 A1* | 1/2011 | Ochs | A61B 5/024 600/300 |
| 2011/0077484 A1 | 3/2011 | Van Slyke et al. | |
| 2013/0272393 A1 | 10/2013 | Kirenko et al. | |
| 2013/0345568 A1* | 12/2013 | Mestha | A61B 5/02405 600/479 |
| 2015/0018693 A1 | 1/2015 | Mestha et al. | |
| 2015/0282724 A1 | 10/2015 | McDuff et al. | |
| 2016/0220128 A1 | 8/2016 | Den Brinker et al. | |
| 2016/0345847 A1* | 12/2016 | Gu | G06F 3/015 |
| 2017/0014040 A1 | 1/2017 | Shim et al. | |
| 2017/0095170 A1* | 4/2017 | Verkruijsse | A61B 5/02416 |
| 2019/0038234 A1* | 2/2019 | De Haan | A61B 5/02416 |
| 2019/0387972 A1* | 12/2019 | Hu | A61B 5/02438 |

FOREIGN PATENT DOCUMENTS

| | | |
|---|---|---|
| WO | 2014024104 A1 | 2/2014 |
| WO | 2015086338 A1 | 6/2015 |

OTHER PUBLICATIONS

Choi et al., "PPG Pulse Direction Determination Algorithm for PPG Waveform Inversion by Wrist Rotation," 39th Annual International Conference of the IEEE Engineering in Medicine and Biology Society (EMBC), Jul. 2017, pp. 4090-4093.

Extended European Search Report from EP Application No. 17188626.0, dated Feb. 9, 2018.

International Search Report and Written Opinion from PCT Application No. PCT/EP2018/071728, dated Oct. 11, 2018.

* cited by examiner

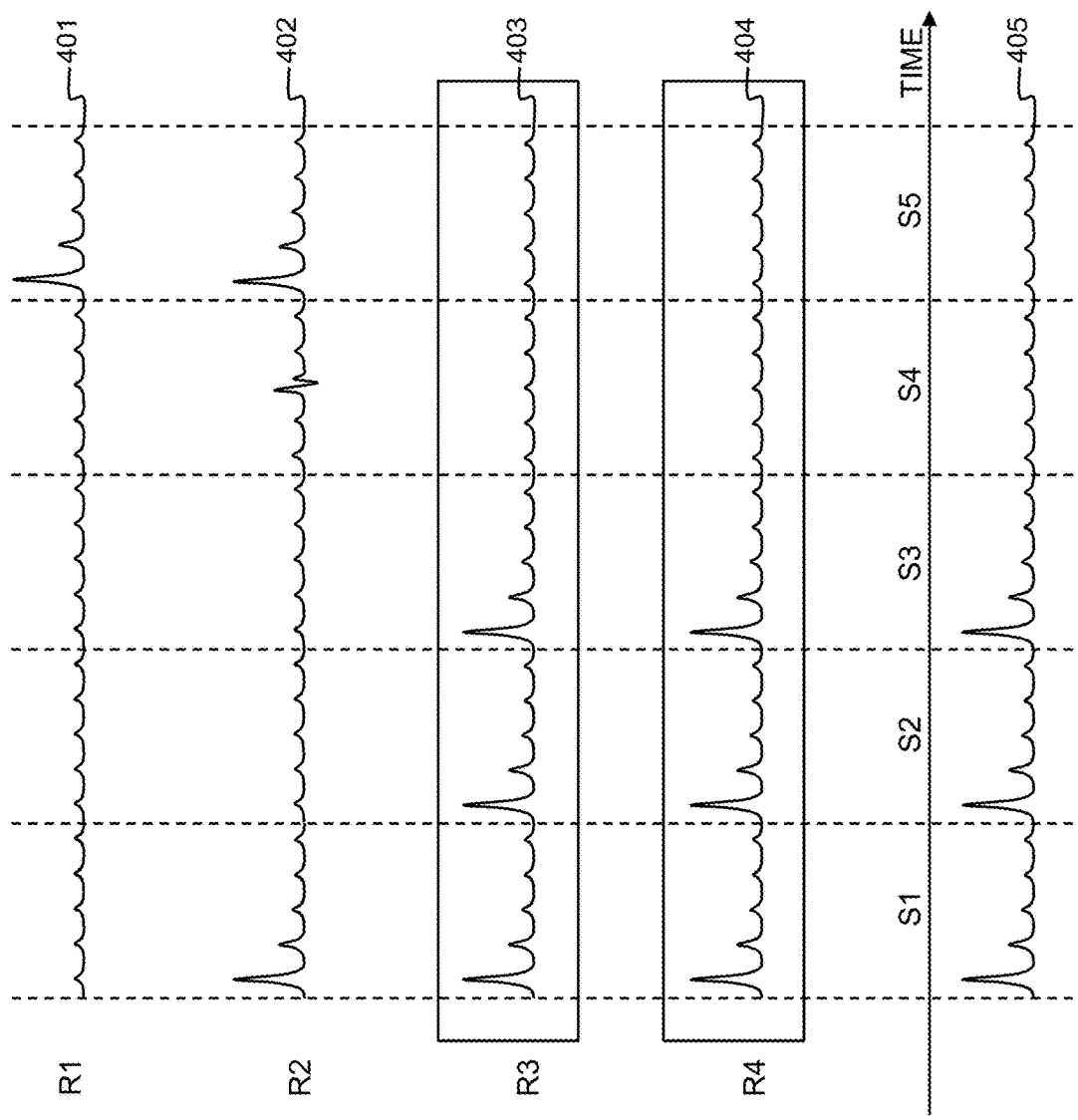
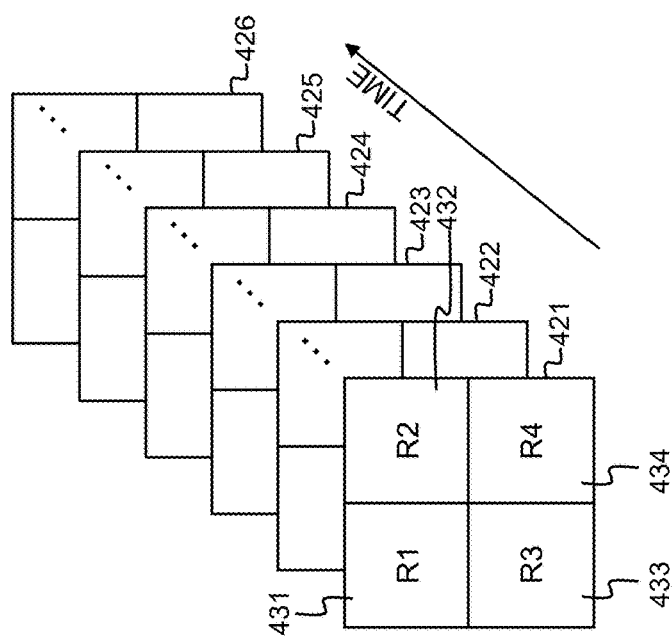
Fig. 4B
Fig. 4A

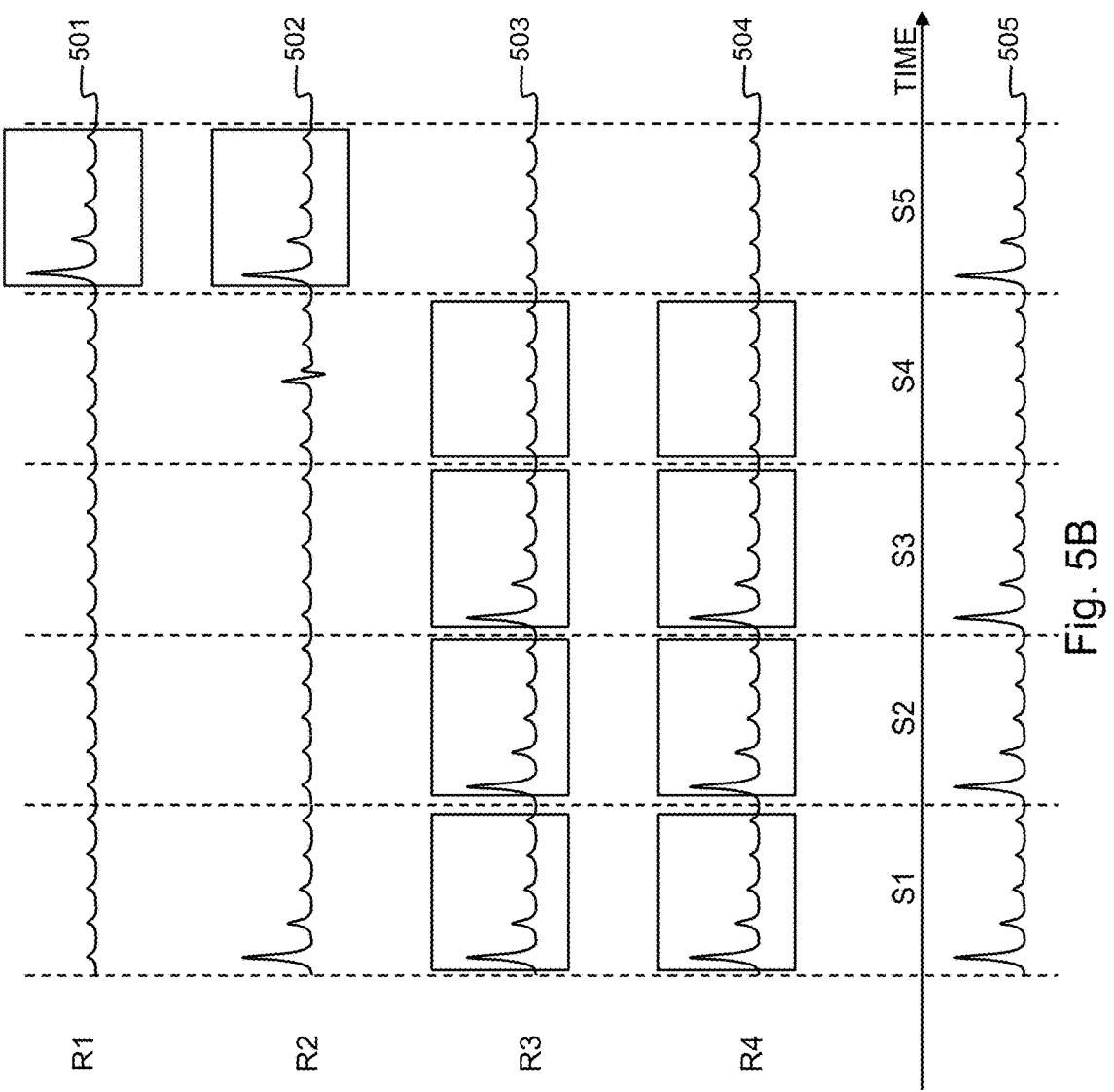
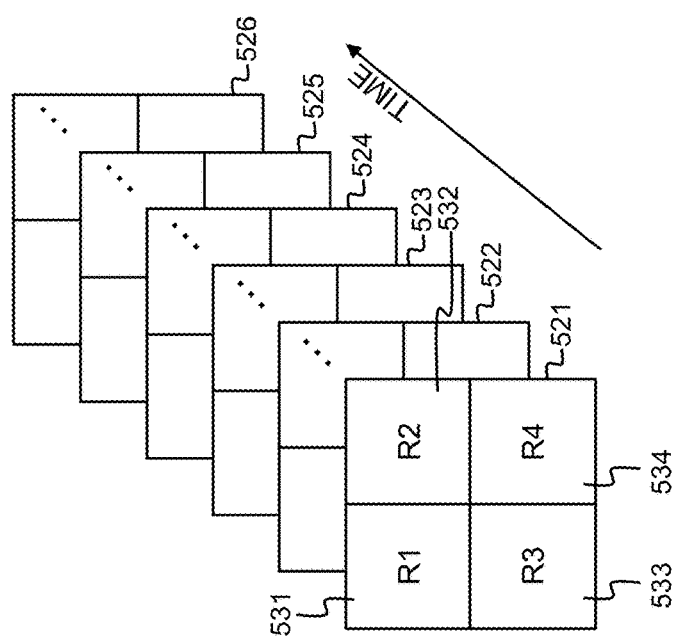
Fig. 5B
Fig. 5A

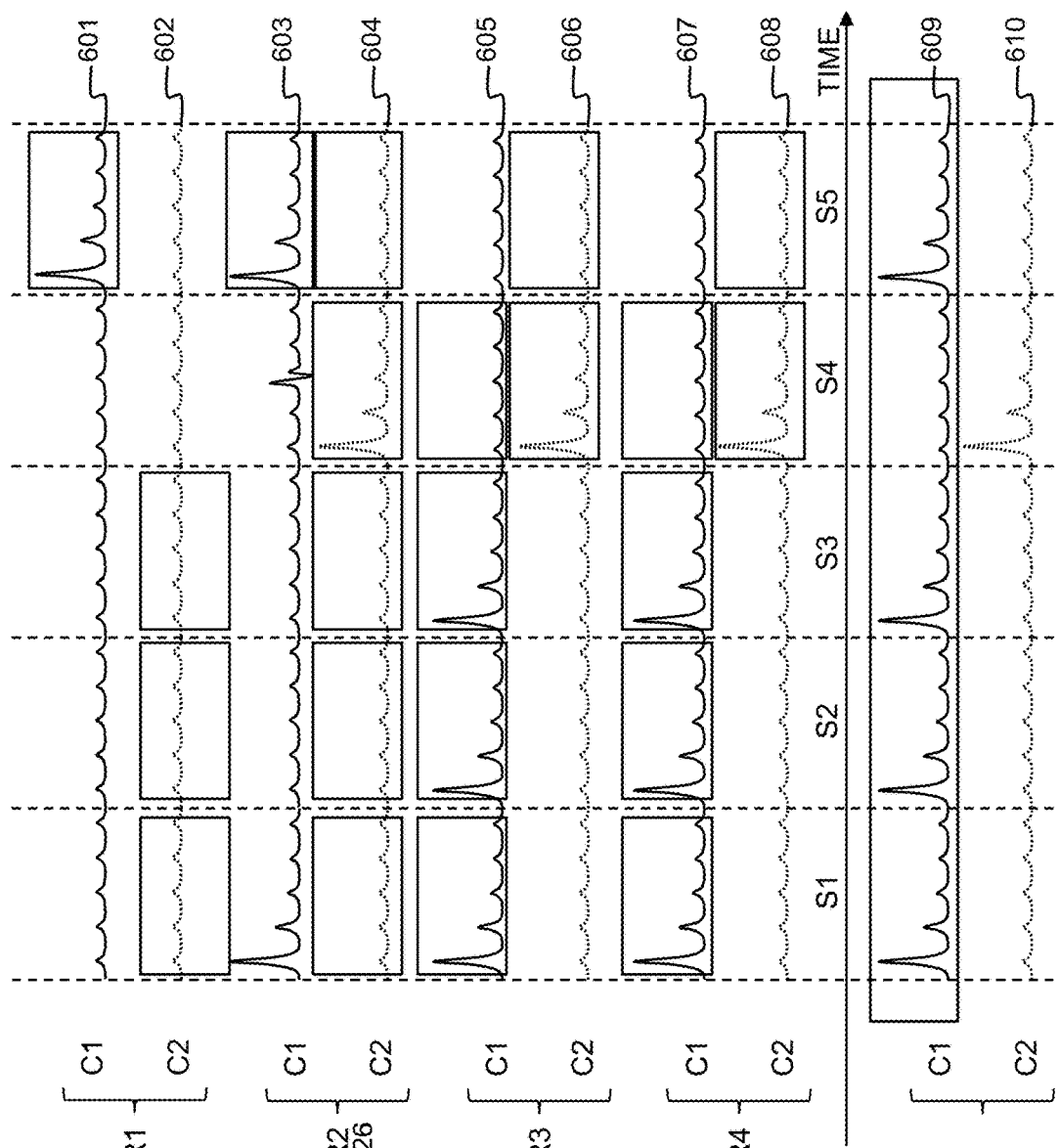
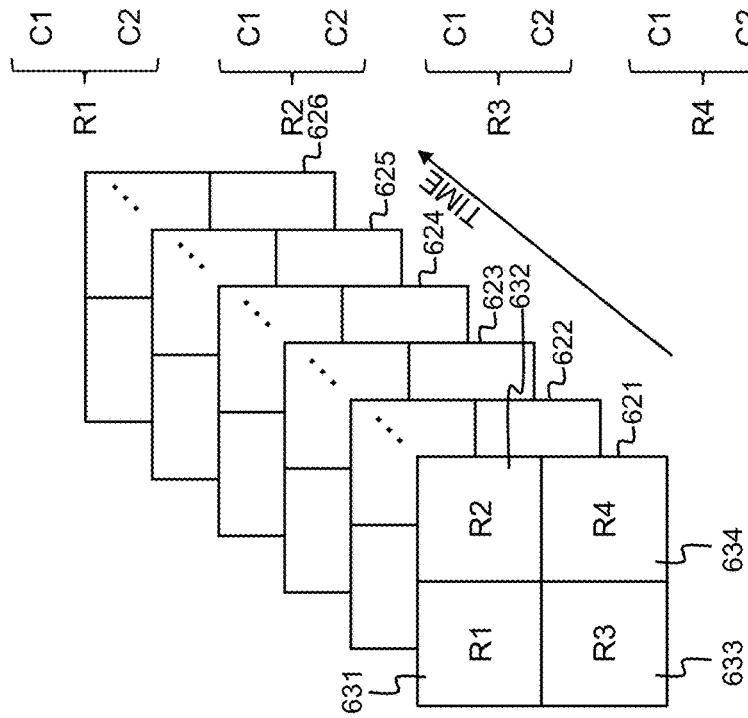
Fig. 6B
Fig. 6A

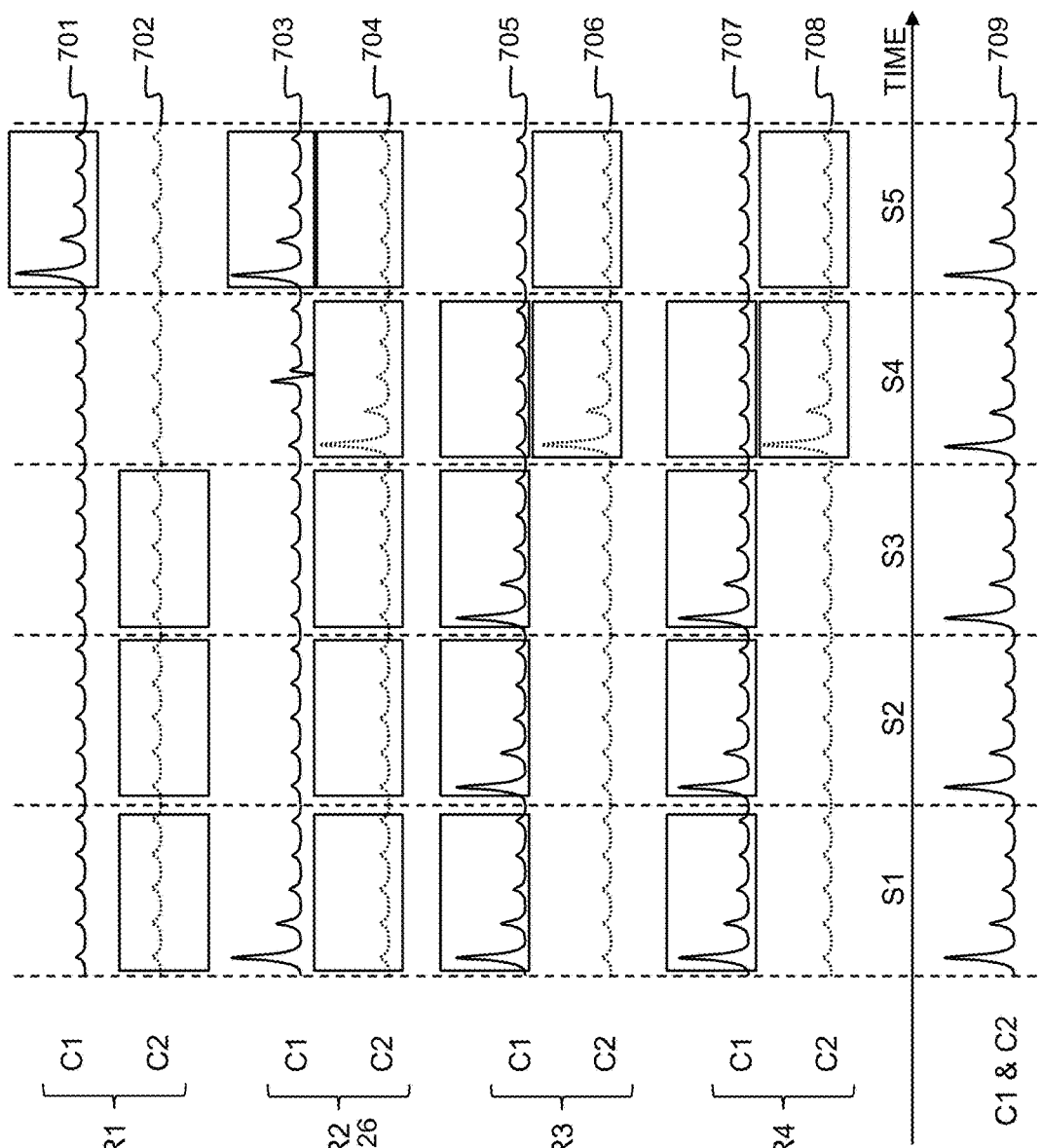
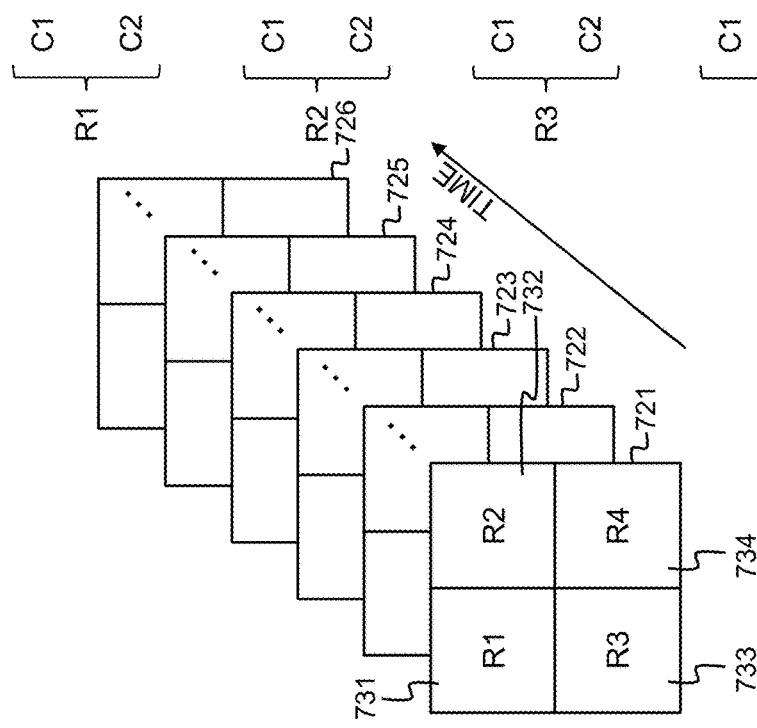
Fig. 7B
Fig. 7A

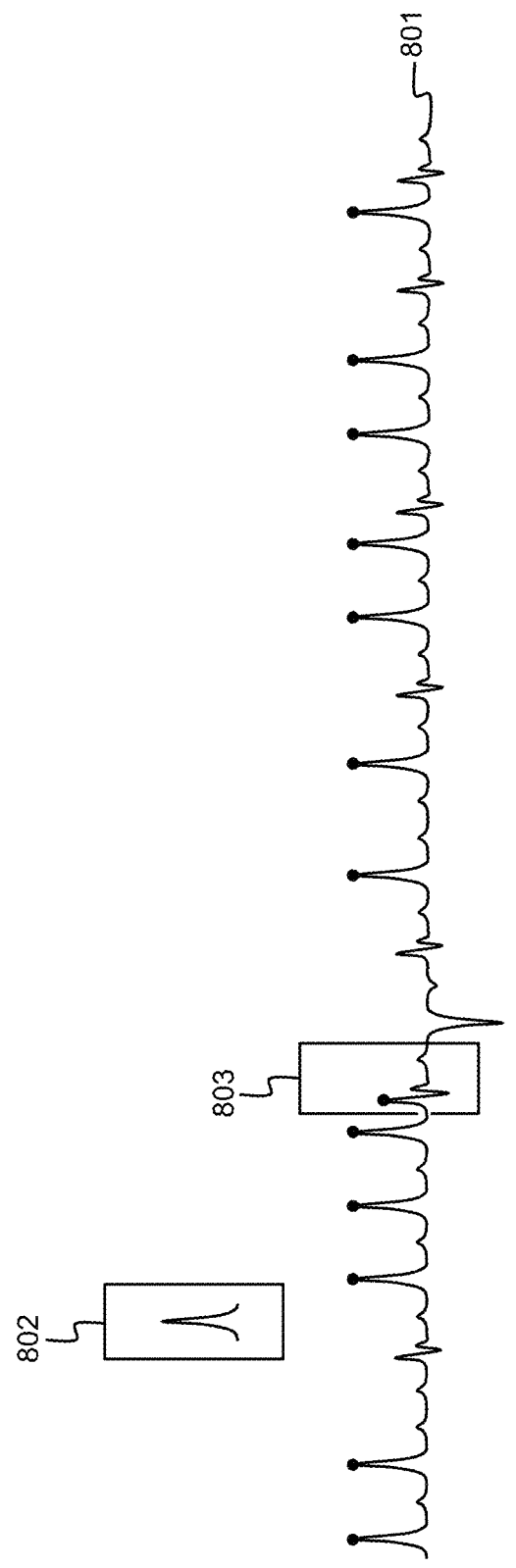

COMPUTER-IMPLEMENTED METHOD AND SYSTEM FOR CONTACT PHOTOPLETHYSMOGRAPHY (PPG)

FIELD OF THE INVENTION

The present invention generally relates to photoplethysmography or PPG, an optical technique to detect blood volume changes that enables to monitor various physiological parameters. The invention more particularly concerns direct PPG or so-called contact PPG wherein the measurement components, i.e. light sources and photodetectors, are in direct contact with the skin of the monitored person. The invention generally envisages to improve the signal quality in contact PPG.

BACKGROUND OF THE INVENTION

Photoplethysmography or PPG is an optical technique that allows to monitor one or more physiological parameters by detecting blood volume changes in peripheral circulation. PPG makes use of light absorption by blood to track these volumetric changes. When a light source illuminates the skin, the reflected light varies as blood flows. A light sensor then converts these variations in light reflection into a digital signal, the so called PPG signal. PPG signals are typically recorded using a pulse oximeter or photodetectors, for instance the camera integrated in an electronic device like a person's smartphone or other smart wearable or non-wearable device.

PPG can be used, among other applications, to monitor cardiovascular and hemodynamic parameters such as heartrate, heartrate variability, blood pressure, or to monitor other physiological variables such as stress, respiration or autonomic functions. One key part of an accurate monitoring with PPG is to obtain a high-quality, artefact-free signal, as PPG can be affected by various sources of noise.

International patent application WO 2014/024104, entitled "Device and Method for Extracting Physiological Information" and filed by Koninklijke Philips N. V., describes a method to improve the accuracy of remote PPG or non-contact-PPG, which is typically used to track a larger region of interest (e.g. a face) in daily applications like fitness. The method divides the region of interest in spatial sub-regions and partitions the PPG signal in signal subsets representing the respective sub-regions. The signal subsets are processed separately. The processing may involve a quality estimation. Thereafter, the signal subsets are combined into an enhanced signal. Distorted sub-signals can be attenuated or eliminated from the combined signal.

Also United States Patent Application US 2013/0272393 A1, entitled "Video Coding and Decoding Devices and Methods Preserving PPG Relevant Information" and filed by Koninklijke Philips N. V., concerns remote PPG.

Although remote PPG is non-obtrusive for the monitored person, it poses major challenges to signal detection and signal processing. As a consequence, the use of remote PPG remains limited to everyday applications like leisure or fitness as its accuracy and reliability are insufficient for medical applications.

As opposed to remote PPG, the present invention concerns contact PPG or contact PPG, wherein the measurement components are in direct contact with the skin in order to obtain a more reliable, more accurate PPG signal that facilitates medical diagnosis.

In applications where a contact PPG signal is processed to determine the heartrate variability, inaccuracies can result from a low signal quality. While a partially good quality signal gives sufficient information to make a reliable analysis, the presence of artefacts can severely affect the quality and can lead to misleading results. Consequently, there is a need to have a contact PPG signal as clean as possible, and to identify and remove bad quality portions to keep only the good quality ones for further analysis.

Artefacts include motion, bad positioning of the skin with respect to the light sensor or ambient light interference. The article "A new look at the essence of the imaging photoplethysmography" from the authors Alexei A. Kamshilin et al. also reports another artifact frequently observed in PPG signals: PPG waveform inversion. This phenomenon is manifested by a signal, or a part of the signal, being inverted in comparison with the usual orientation of the signal. This phenomenon has been observed in adjacent areas of the skin, one area presenting a signal in the usual orientation and the adjacent area presenting a signal in the opposite orientation. This leads to a quality loss of the PPG signal when these two areas are used to extract the signal. Explanations for this phenomenon are still to be validated.

In order to improve the quality of contact PPG signals recorded by means of a camera, it has been suggested to divide the image pixels into a matrix of sub-regions, or quadrants, and to apply a selection algorithm that determines the optimal sub-image, i.e. the quadrant whose PPG signal has the best quality, called the optimal region of interest.

The article "Investigation of Five Algorithms for Selection of the Optimal Region of Interest in Smartphone Photoplethysmography" from authors Rong-Chao Peng et al. describes five algorithms to select the optimal region of interest:

the Variance (VAR) algorithm selects the quadrant whose PPG waveform has the highest variance, i.e. the highest signal power, as optimal region of interest;

the Spectral Energy Ratio (SER) algorithm selects the quadrant whose PPG signal has the highest spectral energy ratio, i.e. which indicates the highest proportion for cardiac activity, as optimal region of interest;

the Template Matching (TM) algorithm selects the quadrant whose PPG signal has the highest similarity with a template waveform as optimal region of interest;

the Temporal Difference (TD) algorithm selects the quadrant whose PPG signal has the highest average intensity variation for pixels between adjacent frames as the optimal region of interest; and the Gradient (GRAD) algorithm selects the quadrant whose PPG signal has the greatest average light intensity gradient as the optimal region of interest.

The article of Peng et al. concludes that the TM and TD algorithms outperform the others in selecting the optimal region of interest and consequently in selecting the PPG signal that enables to estimate physiological parameters with improved accuracy.

The article "Detection of the Optimal Region of Interest for Camera Oximetry" from authors Walter Karlen et al. describes yet another algorithm to determine the preferred quadrant or optimal region of interest. The proposed algorithm considers only blue channels and extracts beats or pulses from the PPG signal through mean pixel intensity calculation and the incremental-merge segmentation (IMS) algorithm. In other words, the selected optimal region of interest has the PPG signal with the highest pulses. Karlen et al. further also teach to select the incandescent white balance mode as preferable setting for PPG on the Samsung Galaxy Ace mobile phone.

In addition to selecting a subset of pixels, the so called optimal region of interest, it has been suggested to generate a PPG signal by choosing a specific color channel. The article "Comparison between red, green and blue light reflection photoplethysmography for heart rate monitoring . . . " from Jihyoung Lee et al. for instance suggests that green light is more suitable for monitoring heartrate.

United States Patent Application US 2011/0077484 A1, entitled "Systems and Methods for Identifying Non-Corrupted Signal Segments for Use in Determining Physiological Parameters" and filed by Assignee Nellcor Puritan Bennett Ireland, teaches to analyse the quality of contact PPG signal segments by processing the wavelet transform of PPG signals with a trained neural network. This results in corrupted and non-corrupted PPG signal segments being identified. Corrupted signal segments are removed or replaced by earlier received, non-corrupted PPG signal segments.

The known solutions rely on the selection of a single region of interest and extract the PPG signal from this selected region of interest. However, the selected region of interest is static, i.e. the optimal region is a single sub-region of pixels that is considered to be the same for the whole measurement. Useful information in other sub-regions is not used. This can lead to unsatisfying results when the optimal sub-region to extract the PPG signal varies across the measurement. The extracted PPG signal may then contain inversions and/or bad quality sections that reduce the accuracy of physiological parameter estimation, e.g. the accuracy of heart rate variability, and consequently the accuracy of any disease diagnosis, for instance AF diagnosis, built thereon.

Likewise, the color selection in known systems for contact PPG signal extraction is made beforehand and the same color is statically used for every analysis.

Furthermore, none of the prior art solutions aimed at improving signal quality target the camera settings that may negatively influence the contact PPG signal quality across various vendors and types of smart devices.

It is therefore an objective of the present invention to disclose a computer-implemented method for contact PPG that resolves one or more of the above-identified shortcomings of existing solutions. More particularly, it is an objective to disclose a method for contact PPG with improved accuracy and reliability.

SUMMARY OF THE INVENTION

According to the present invention, the above identified objective is realised by the computer-implemented method for contact photoplethysmography, abbreviated contact PPG, as defined by claim 1, comprising:

obtaining during a time interval plural PPG signals for respective sub-regions of a lens or video frame, each sub-region of the sub-regions covering multiple pixels; and combining the plural PPG signals to thereby obtain a multi-region PPG signal.

Thus, multiple contact PPG signals that are spatially segmented, i.e. obtained from different multi-pixel sub-regions of the lens used for contact PPG, are combined into a multi-region PPG signal. Thanks to the combining of PPG signals of multiple sub-regions, good quality PPG information is not eliminated through static upfront selection of a single spatial sub-region and/or static upfront selection of a single color. Good quality portions of the different PPG signal will be present in the multi-region PPG signal, hence increasing the presence of valuable information in the multi-region PPG signal, as well as the accuracy and reliability of any physiological parameter estimation derived therefrom.

It is noticed that each PPG signal in the method according to the present invention represents a direct PPG signal or contact PPG signal obtained for a spatial segment or sub-region of the lens. The spatial segment or sub-region represents multiple pixels. If for instance the lens surface is divided in four sub-regions, each sub-region represents a quadrant of the lens.

It is further noticed that the time interval in the method according to the present invention corresponds to a time interval during which a continuous contact PPG measurement is carried out. The time interval shall typically range from a few tens of seconds, e.g. 30 seconds, up to a few minutes, e.g. 3 minutes. Thus, the time interval may for instance correspond to the length of a video frame of 60 seconds if an AF patient is requested to make a 1 minute PPG measurement twice a day for monitoring purposes.

In line with the present invention, the PPG signals obtained during such time interval from different spatial sub-regions may be combined statically into the multi-region PPG signal or they may be combined dynamically into the multi-region PPG signal. Statically combining sub-region PPG signals implies that the sub-region PPG signals are combined in the same manner during subsequent time intervals. Statically combining the PPG signals of multiple sub-regions may for instance be obtained by averaging the sub-region PPG signals, or by adding or averaging sub-region PPG signals of a particular subset of sub-regions. When statically combining the sub-region PPG signals, the sub-region PPG signals may be combined in a different manner in subsequent time intervals. As an example, static multi-region PPG may involve making an assessment and depending on that assessment adding PPG signals of a first subset of sub-regions in a first time interval whereas PPG signals of a second subset of sub-regions, different from the first subset, are added in a second time interval based on a new assessment that was made for the second time interval PPG signals, herewith anticipating inter-measurement differences. This may for instance be advantageous if the assessment reveals that the sub-regions that deliver good quality PPG signals vary over time. Dynamically combining the PPG signals is realized by combining PPG signals of different subsets of sub-regions in different temporal sub-segments of the time interval, to anticipate intra-measurement differences, as will be explained further below.

It is further noticed that within a time interval, PPG signals obtained for different colors may be selected or combined, and the colors that are selected or combined may vary between spatial sub-regions, as will be further explained below.

Embodiments of the computer-implemented method for contact PPG according to the present invention, as defined by claim 2, further comprise:

processing each PPG signal of the plural PPG signals to identify good quality segments of the PPG signal wherein a quality measure of the PPG signal is above a threshold and bad quality segments of the PPG signal wherein the quality measure of the PPG signal is below the threshold;

removing the bad quality segments from each PPG signal of the plural PPG signals; and combining temporal corresponding good quality segments of the plural PPG signals to obtain the multi-region PPG signal.

Indeed, advantageous embodiments of the present invention implement dynamic multi-region PPG with temporal segmentation. PPG signals are obtained for plural spatial segments or sub-regions of the lens or video frame. Each of these PPG signals is segmented into time segments with a typical length of a few seconds. If PPG signals are obtained for a time interval of 60 seconds, these PPG signals may for instance be segmented into twelve time segments of 5 seconds each. The segmentation is identical for all PPG signals such that for each segment in a PPG signal, temporally corresponding segments exist in the PPG signals obtained for other sub-regions. Each PPG signal segment is then subjected to a quality assessment. According to some quality measure, a distinction is made between good quality PPG signal segments and bad quality PPG signal segments, i.e. PPG signal segments for which the quality assessment exceeds a given quality threshold and PPG signal segments for which the quality assessment stays below the given threshold. The bad quality PPG signal segments are eliminated, i.e. they are removed from the respective PPG signals. The good quality segments of the different sub-region PPG signals that temporally correspond with each other are combined: such segments are for instance added, or a weighted sum of such segments is made wherein the weights are proportional to the respective quality value determined for such segments, or alternative combinations may be considered as will be appreciated by the person skilled in the art. As a result, a multi-region PPG signal is composed that performs even better in terms of accuracy and reliability because it combines only the good quality portions of the PPG signals and leaves bad quality portions of the PPG signals out of the multi-region PPG signal.

In embodiments of the computer-implemented method for contact PPG according to the present invention, as defined by claim 3, the good quality segments comprise non-inverted segments and inverted segments, and the processing of each PPG signal further comprises identifying the inverted segments and reverting the inverted segments.

Indeed, inverted PPG signals can be maintained as good quality PPG signals after being reversed. In advantageous embodiments of the method according to the invention, the quality assessment distinguishes between good quality non-inverted PPG signal segments, inverted PPG signal segments and bad quality PPG signal segments. This may for instance be achieved by inverting each of the PPG signal segments, applying the quality measure and verifying if the quality measure exceeds the given threshold. If this is the case, the PPG signal segment is an inverted PPG signal segment that can be maintained for the multi-region PPG signal composition on the condition it is reverted to become a non-inverted, good quality PPG signal. Reverting the PPG signal segment boils down to changing the sign of the samples. By reverting inverted PPG signal segments and maintaining such PPG signal segments for the composition of the multi-region PPG signal, the accuracy and reliability of the latter multi-region PPG signal is further enhanced.

In further embodiments of the computer-implemented method for contact PPG according to the present invention, as defined by claim 4, the processing of each PPG signal comprises:
  wavelet transforming the PPG signal to obtain a wavelet transformed PPG signal; and
  supplying the wavelet transformed PPG signal to a neural network trained to identify good quality segments of the PPG signal and bad quality segments of the PPG signal.

Thus, preferred embodiments of the invention wavelet transform the PPG signal segments. The wavelet transformed PPG signal segments are then supplied to a neural network that has been trained with sample sets to distinguish good quality signal segments and bad quality signal segments. The skilled person however will appreciate that alternative quality measures exist to distinguish good quality PPG signal portions from bad quality PPG signal portions that do not rely on wavelet transformation and/or neural networks.

In further embodiments of the computer-implemented method for contact PPG according to the invention, as defined by claim 5, the neural network is further trained to identify the inverted segments.

Indeed, the neural network is preferably also trained to distinguish inverted PPG signal segments. These inverted PPG signal segments may then be reverted to become good quality PPG signal segments retained for the multi-region PPG signal composition.

Embodiments of the computer-implemented method for contact PPG according to the present invention, as defined by claim 6, comprise:
  generating plural multi-region PPG signals similar to the multi-region PPG signal for respective colors from a color space.

Indeed, optionally, the sub-region PPG signals are obtained for different colors of a color space, for instance red, green and blue in the RGB space or cyan, yellow, and magenta in the CYMK space. The sub-region PPG signals obtained for a single color, e.g. green, may then be combined into a multi-region PPG signal for that color. This way, multi-region PPG signals can be generated for the respective colors of the color space. The multi-region PPG signal of the color with highest quality may then be selected statically or dynamically as will be explained below.

Embodiments of the computer-implemented method for contact PPG according to the present invention, as defined by claim 7, further comprise:
  determining a quality measure for each one of the colors; and
  selecting amongst the plural multi-region PPG signals the multi-region PPG signal for the color with highest quality measure.

Thus, advantageous embodiments of the invention produce multi-region PPG signals for plural colors of a color space, and statically select a single multi-region PPG signal of a single color based on a quality assessment. The selected multi-region PPG signal of a single color is then used for physiological parameter estimation. For the next time interval, it is however possible that the multi-region PPG signal of a different color is selected.

Alternative embodiments of the computer-implemented method for contact PPG according to the present invention, as defined by claim 8, further comprise:
  determining a quality measure for each one of the colors; and
  combining multi-region PPG signals for plural colors into a multi-color multi-region PPG signal.

Indeed, as an alternative to selecting a single color, the multi-region PPG signals of different colors may be combined provided that the phase-shift that is existing between PPG signals obtained for different colors, is compensated for.

Embodiments of the computer-implemented method for contact PPG according to the invention, as defined by claim 9, further comprise:
  obtaining during the time interval plural PPG signals for respective colors and respective sub-regions;
  processing each PPG signal of the plural PPG signals to identify good quality segments of the PPG signal wherein a quality measure of said PPG signal is above a threshold and bad quality segments of the PPG signal wherein the quality measure of the PPG signal is below the threshold;

removing the bad quality segments from each PPG signal of the plural PPG signals; and combining temporal corresponding good quality segments of the plural PPG signals to obtain the multi-color multi-region PPG signal.

Hence, advanced embodiments of the invention segment each sub-region PPG signal into time segments with a typical length of a few seconds, e.g. 5 seconds. This is done for each color. The individual PPG signal segments are processed to assess the quality thereof. They may for instance be wavelet transformed and fed into a neural network that distinguishes good quality segments, bad quality segments and possibly inverted segments. Bad quality segments are eliminated, and good quality segments that temporally correspond are combined across the sub-regions and across the colors in order to dynamically generate a multi-color multi-region PPG signal wherein each segment may be composed of different colors and different sub-regions. The so-obtained multi-color multi-region PPG signal is optimal in terms of accuracy and reliability as it dynamically combines the best of colors with the best of sub-regions while eliminating all PPG signal portions of poor quality.

Embodiments of the computer-implemented method for contact PPG according to the present invention, as defined by claim 10, further comprise locking settings of the lens during the time interval, the settings at least comprising:

diaphragm; and light sensitivity or light exposure.

Indeed, in order to reduce the amplitude noise and consequently improve the accuracy and reliability of the PPG signals, the camera settings are preferably locked during the full PPG video frame time interval. The camera settings that are preferably locked at least must include the diaphragm and the light sensitivity or light exposure. Other camera settings like for instance the brightness may however also be locked during the complete PPG video frame time interval in order to further reduce noise and further improve the accuracy of PPG measurements. It is noticed that locking the camera settings brings advantages in noise reduction and accuracy independent from the multi-region PPG signal composition. Thus, also in situations where no plural sub-region PPG signals are combined to compose a multi-region PPG signal and/or in situations where no plural colors are combined to compose a multi-color PPG signal, the locking of camera settings during PPG signal acquierement brings substantial advantages in amplitude noise reduction.

Embodiments of the computer-implemented method for contact PPG according to the present invention, as defined by claim 11, further comprise detecting peaks in the multi-region PPG signal, and thereto:

detecting initial peaks in the multi-region PPG signal;

windowing the initial peaks in the multi-region PPG signal to thereby generate windowed initial peaks;

averaging the windowed initial peaks in the multi-region PPG signal to thereby generate a peak template;

correlating the initial peaks with the peak template;

maintaining initial peaks for which a correlation measure exceeds a correlation threshold as peaks; and dropping initial peaks for which the correlation measure does not exceed the correlation threshold.

Thus, preferred embodiments of the present invention apply a template matching peak detection algorithm to detect peaks in the composed multi-region PPG signal. In a first step, initial amplitude peaks are detected in the multi-region PPG signal. Each initial peak is windowed through a window that filters a limited set of samples preceding the detected initial peak and a limited set of samples following the initial peak out of the multi-region PPG signal. The so-obtained windowed initial peaks are then averaged to compose a peak template that corresponds to the average initial peak. Each one of the detected initial peaks is thereafter compared or correlated with the template peak and initial peaks whose correlation with the template peak stays below a predetermined threshold are eliminated, i.e. they are no longer considered to constitute peaks. The template matching peak detection algorithm may be repeated iteratively, possibly with increasing correlation threshold, until all peaks satisfy a final, desired correlation threshold. The final set of peaks may then be used for physiological parameter estimation.

Embodiments of the computer-implemented method for contact PPG according to the present invention, defined by claim 12, further comprise:

extracting an RR-tachogram by determining a time difference between subsequent peaks in the multi-region PPG signal.

Thus, embodiments of the invention suitable for applications wherein the heartbeat or heartrate is monitored or analysed further may extract an RR-tachogram from the peaks determined in the multi-region PPG signal. The timing of the maintained peaks thereto is considered. The time difference between each two subsequent peaks is determined to compose the RR-tachogram.

Embodiments of the computer-implemented method for contact PPG according to the invention, defined by claim 13, further comprise:

processing the multi-region PPG signal to identify good quality segments of the multi-region PPG signal wherein a quality measure of the multi-region PPG signal is above a threshold and bad quality segments of the multi-region PPG signal wherein the quality measure of the multi-region PPG signal is below said threshold;

removing peaks within the bad quality segments from the multi-region PPG signal before extracting the RR-tachogram; and removing from the RR-tachogram the RR-tachogram intervals located totally or partially within the bad quality segments of the multi-region PPG signal.

Thus, the RR-tachogram may be processed to contain exclusively the RR-tachogram intervals that lie within good quality intervals of the multi-region PPG signal. Thereto, the quality of segments of the multi-region PPG signal must be assessed according to measure to distinguish good quality segments from bad quality segments in the multi-region PPG signal. The quality assessment may be identical or similar to the quality assessment used for the individual PPG signals, for instance based on wavelet transforming and neural network analysis, but alternative quality measures may be applied as well, as will be appreciated by the person skilled in the art. The quality assessment results in an identification of good quality segments and bad quality segments in the multi-region PPG signal that is thereafter used to eliminate peaks that passed the peak detection algorithm but which are located in a bad quality segment of the multi-region PPG signal from this multi-region PPG signal. Consequently, also the RR-tachogram intervals that are located entirely or partially within such bad quality intervals of the multi-region PPG signal are removed from the RR-tachogram to obtain an RR-tachogram with improved reliability.

Embodiments of the computer-implemented method for contact PPG according to the present invention, as defined by claim 14, further comprise:
  determining a variability in the time difference between subsequent peaks; and
  determining from the variability an atrial fibrillation risk score.

Embodiments of the invention suitable for atrial fibrillation (AF) risk analysis further determine the variability in the time difference between subsequent peaks maintained by the peak detection algorithm, i.e. the heartbeat variability or heartrate variability. An AF score is determined proportional to this variability and when this AF score exceeds a predefined threshold the patient or monitored person may be warned such that a clinician can be consulted for further diagnosis.

In addition to a computer-implemented method as defined by claims 1-14, the present invention also concerns a corresponding computer program product as defined by claim 15, comprising computer-executable instructions for performing the method when the program is run on a computer.

The present invention further also concerns a computer readable storage medium as defined by claim 16, comprising the computer program product.

The present invention further also concerns a data processing system as defined by claim 17, programmed for carrying out the method according to one of claims 1-14.

BRIEF DESCRIPTION OF THE DRAWINGS

FIG. 4A and FIG. 4B illustrate the step of combining plural PPG signals into a multi-region PPG signal in embodiments of the computer-implemented method for contact PPG according to the present invention that implement static multi-region PPG;

FIG. 5A and FIG. 5B illustrate the step of combining plural PPG signals into a multi-region PPG signal in embodiments of the computer-implemented method for contact PPG according to the present invention that implement dynamic multi-region PPG;

FIG. 6A and FIG. 6B illustrate the step of combining plural PPG signals into a multi-region PPG signal in embodiments of the computer-implemented method for contact PPG according to the present invention that implement dynamic multi-region PPG with color selection;

FIG. 7A and FIG. 7B illustrate the step of combining plural PPG signals into a multi-region PPG signal in embodiments of the computer-implemented method for contact PPG according to the present invention that implement dynamic multi-region multi-color PPG;

FIG. 8 illustrates the step of peak detection in embodiments of the computer-implemented method for contact PPG according to the present invention that implement template based peak selection;

DETAILED DESCRIPTION OF EMBODIMENT(S)

Figure 1:
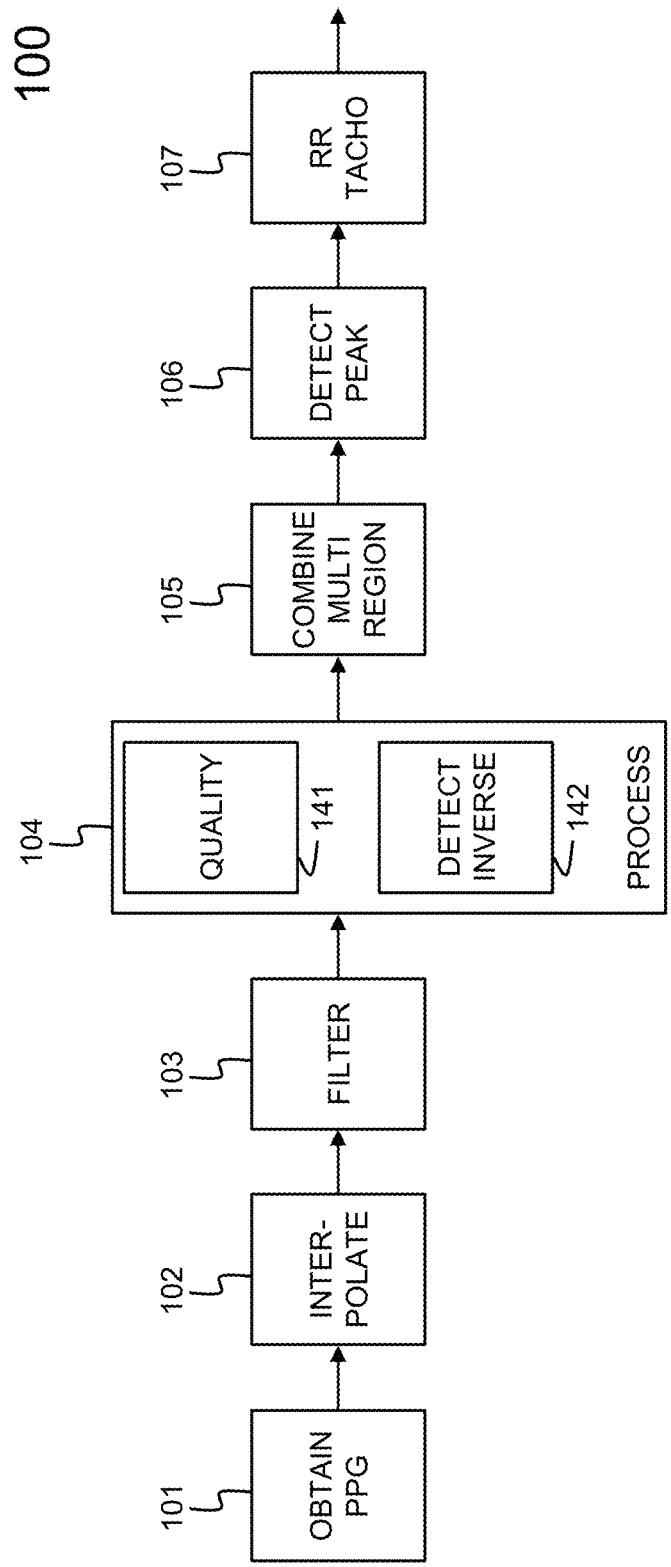
FIG. 1 is a block scheme illustrating an embodiment of the computer-implemented method for contact PPG according to the present invention.

FIG. 1 shows the steps subsequently executed in an embodiment 100 of the method for contact PPG or direct PPG according to the present invention. In a first step 101, plural PPG signals are obtained for respective sub-regions of a canvas. The canvas may for instance be a lens of a camera integrated in an electronic device. Alternatively, the canvas may be a video frame representing the pixels obtained at a single point in time as a result of some imaging operation. Each PPG signal obtained in step 1 represents a sub-region of the canvas, i.e. a subset of plural neighbouring pixels, like for instance a quadrant of the canvas. The PPG signals are obtained for a single color, or alternatively PPG signals may be obtained for plural colors, e.g. R, G and B colors or C, M and Y colors in each of the sub-regions. The PPG signals are obtained during a predefined time interval that typically is set from a few tens of seconds up to a few minutes. The PPG signals are obtained at an exemplary frequency of 30 Hz, meaning that 30 images per second are taken by the imaging device to serve as basis for the PPG signals. Tests have demonstrated that it is of importance that certain settings of the camera or imaging device are locked during the time interval wherein the PPG signals are obtained, because locking the camera settings substantially improves the quality of the PPG signals. These settings at least comprise the diaphragm and the light sensitivity or light exposure. In case the PPG signals are obtained by a wearable device, e.g. the camera integrated in a smartphone, it may therefore be advised to remotely control the camera settings to stay locked during the execution of step 101.

In a second step 102, interpolation is performed between video frames to ensure an equal sampling of all video frames. Thereafter, in step 103, each PPG signal is filtered, typically bandpass filtered to remove noise and obtain PPG signals within the frequency band of interest. The frequency band of interest may be determined by the medical application. In case of heartbeat, heartrate or heartrate variation analysis, the frequency band of interest for instance is a frequency band ranging from 30 Hz to 200 Hz. It is noticed that the step 101 of obtaining PPG signals, the interpolation step 102 and the filtering step may jointly form part of pre-processing that is executed remotely, e.g. on the smartphone or other electronic device worn by the person whereon contact PPG is applied. Subsequent steps 104-107 that will be explained in the following paragraphs but generally are more processing intensive, shall typically be executed centrally, i.e. on a server with higher processing capacity, although it is not excluded that certain steps or sub-steps in future embodiments of the invention also may be executed remotely on electronic devices since processing power of such electronic devices continues to grow.

In step 104, each PPG signal is processed. The processing involves both assessing the quality in sub-step 141 and detecting inversion in sub-step 142. Assessing the quality and detecting inversion may be applied for the entire PPG signal over the entire time interval in static implementations of the invention. Alternatively, the quality assessment and inversion detection is applied on time segments of the PPG signal in dynamic implementations of the invention. As a result good quality portions and bad quality portions are identified in the PPG signal. Portions of the PPG signal that are inverted, are reverted to become good quality portions that remain useful. Bad quality portions shall be removed from the PPG signal.

In step 105, plural PPG signals obtained for different sub-regions are combined into a multi-region PPG signal, i.e. an artificially composed PPG signal that contains information extracted from plural PPG signals representing plural sub-regions of the image canvas. Obviously, the good quality portions of plural sub-region PPG signals are combined into a single multi-region PPG signal that performs better in terms of accuracy and reliability for subsequent physiological parameter extraction. In static implementations of the invention, entire PPG signals of different sub-regions found to have good quality, either of a single color or of multiple synchronized colors, are combined into a single multi-region PPG signal. In dynamic implementations of the invention, temporally corresponding segments of plural PPG signals are combined. The set of PPG signal segments that is combined typically varies from segment to segment, i.e. different sub-regions and/or different colors may be represented in different segments of the multi-region PPG signal because the quality of the different colors and the quality of the different sub-regions varies in time.

To the so composed multi-region PPG signal, a peak detection algorithm is applied in step 106 in order to detect peaks, and the inter-peak distance is determined in step 107 in order to extract an RR-tachogram, useful in analysis of the heartrate variability and AF risk level of a patient. Obviously, steps 106 and 107 may not be executed in embodiments of the invention that implement contact PPG for other purposes than heartbeat, heartrate or heartrate variability analysis.

Figure 2:
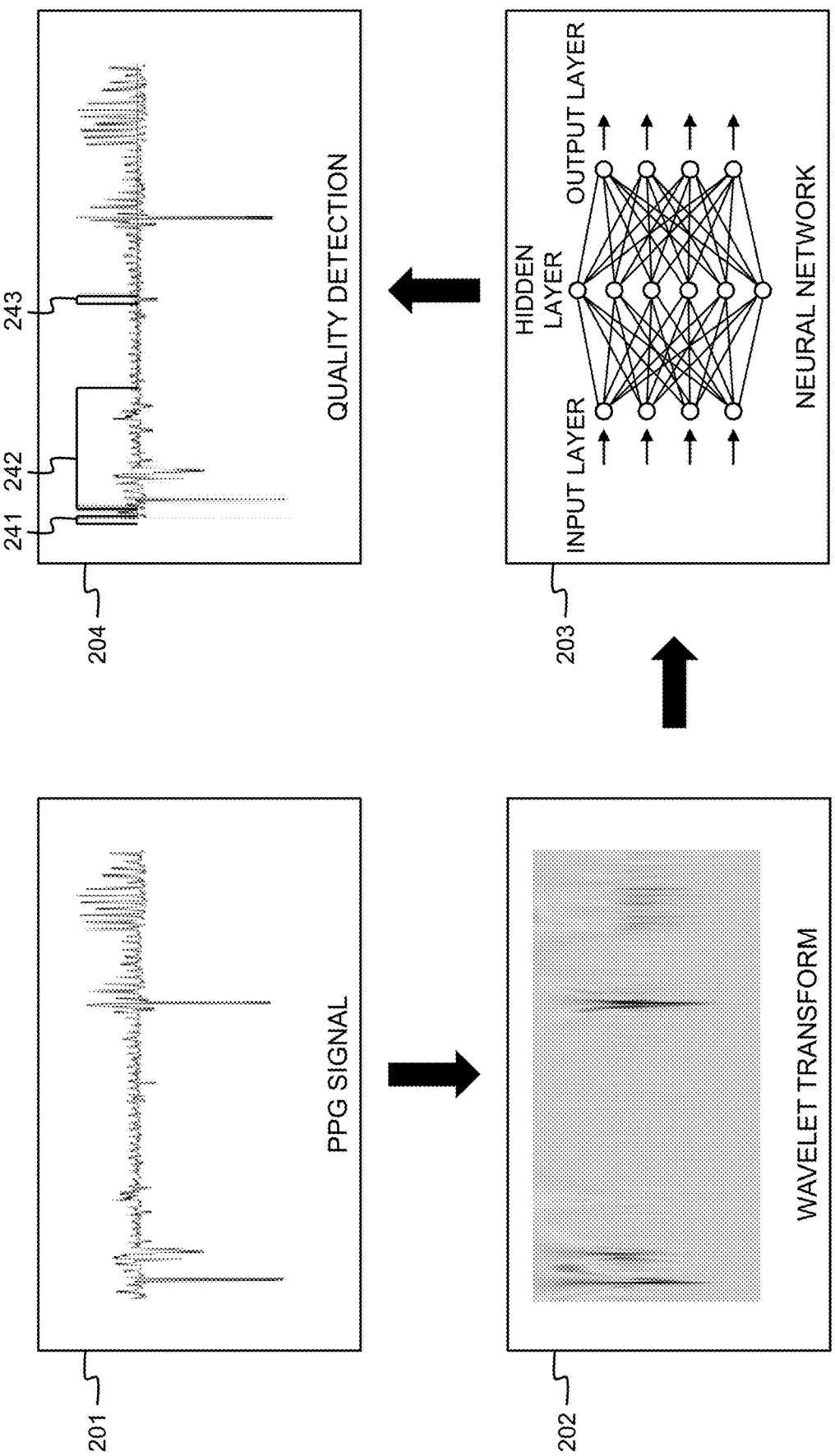
FIG. 2 illustrates the step of processing a PPG signal for quality assessment in embodiments of the computer-implemented method for contact PPG according to the present invention.

FIG. 2 illustrates the operation of step 104, i.e. the quality assessment and inversion detection, as executed in embodiments of the invention. Each sub-region PPG signal 201 is wavelet transformed thus resulting in the wavelet transformed sub-region PPG signal 202. This wavelet transformed PPG signal 202 is then fed into a neural network 203 that has been trained with sets of training data to distinguish good quality PPG signals, bad quality PPG signals, and inverted PPG signals. The outcome of the neural network 203 is that the sub-region PPG signal is either qualified as good quality PPG signal, bad quality PPG signal, or inverted PPG signal. In the latter case, the PPG signal is reverted and the reverted PPG signal is qualified as good quality PPG signal. In dynamic implementations of the present invention, the quality assessment based on wavelet transformation and neural network analysis is performed for each segment of each sub-region PPG signal. As a result thereof, good quality portions are identified in the PPG signal 201 and bad quality portions 241, 242, 243 are identified in the PPG signal 201. The bad quality portions 241, 242, 243 at last are removed from the PPG signal 204. Likewise, in implementations of the invention wherein multiple colors are considered, the quality assessment and inversion detection described here above with reference to FIG. 2 may be applied to a single color if an upfront selection is made of a single color for instance as a result of a different quality assessment used for selecting the best color, may be applied for the entire PPG signals of plural colors in order to be able to statically combine good quality colors into a multi-color multi-region PPG signal, or may be applied to segments of plural colors in order to be able to dynamically combine sub-regions and colors into a multi-color multi-region PPG signal.

Figure 3:
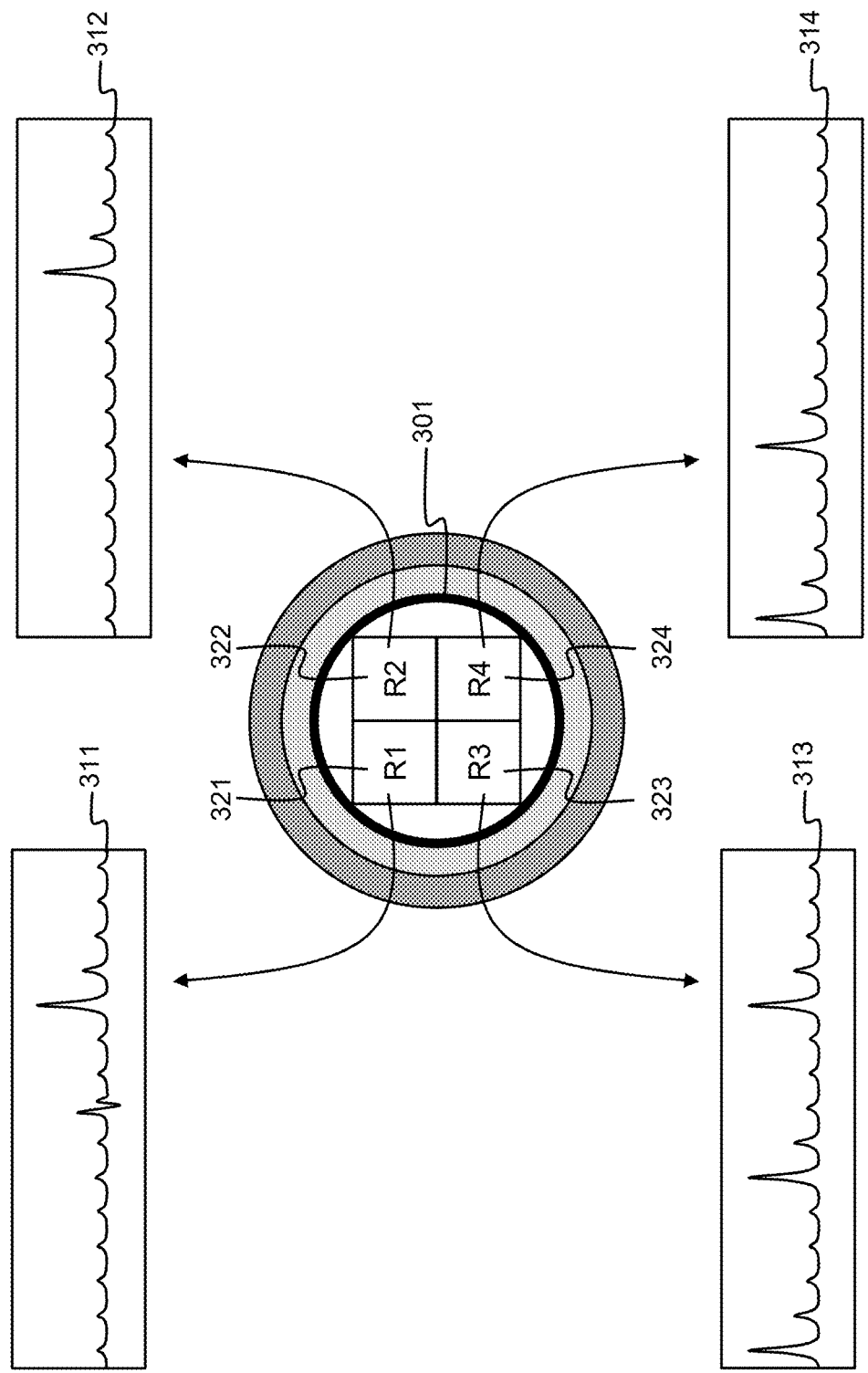
FIG. 3 illustrates the step of obtaining plural PPG signals for plural sub-regions in embodiments of the computer-implemented method for contact PPG according to the present invention.

FIG. 3 illustrates in more detail step 101 of obtaining plural PPG signals 311, 312, 313 and 314, respectively representing different sub-regions 321, 322, 323 and 324 of a lens 301 of a camera. In FIG. 3, the lens area is subdivided into 4 quadrants: R1 or 321, R2 or 322, R3 or 323 and R4 or 324. Each of these quadrants corresponds to a different sub-region representing plural neighbouring pixels in the captured video frames or images. The pixels in the upper left quadrant, R1 or 321, of the lens 301 are used to obtain a first PPG signal 311. The pixels in the upper right quadrant, R2 or 322, of the lens 301 are used to obtain a second PPG signal 312. The pixels in the lower left quadrant, R3 or 323, of the lens 301 are used to obtain a third PPG signal 313. The pixels in the lower right quadrant, R4 or 324, of the lens 301 are used to obtain a fourth PPG signal 314. The obtained PPG signals 311, 312, 313 and 314 differ because they result from light reflections in different parts of the body, and because of various artefacts like inversions. In line with the present invention, the sub-region PPG signals 311, 312, 313 and 314 will be combined into a single multi-region PPG signal with improved reliability and accurateness over the individual sub-region PPG signals 311, 312, 313 and 314. With reference to FIG. 4A-4B, FIG. 5A-5B, FIGS. 6A-6B and FIG. 7A-7B, the following paragraphs will describe different ways of combining the sub-region PPG signals into a multi-region PPG signal.

FIG. 4A shows five video frames 421 . . . 422 . . . 423 . . . 424 . . . 425 . . . 426, taken at subsequent time moments by a lens similar to lens 301 in FIG. 3. Each video frame 421 is subdivided in four quadrants or sub-regions 431, 432, 433 and 434 respectively corresponding to sub-regions R1, R2, R3 and R4 of the lens. From the pixels of the first sub-region, 431 or R1, a first PPG signal 401 is obtained. The respective segments S1, S2, S3, S4 and S5 of this PPG signal 401 are obtained respectively from the first quadrant pixels in the video frames 421 . . . 422 (excluding 422), 422 . . . 423 (excluding 423), 423 . . . 424 (excluding 424), 424 . . . 425 (excluding 425) and 425 . . . 426 (excluding 426). From the pixels of the second sub-region, 432 or R2, a second PPG signal 402 is obtained. The respective segments S1, S2, S3, S4 and S5 of this PPG signal 402 are obtained respectively from the second quadrant pixels in the video frames 421 . . . 422 (excluding 422), 422 . . . 423 (excluding 423), 423 . . . 424 (excluding 424), 424 . . . 425 (excluding 425) and 425 . . . 426 (excluding 426). From the pixels of the third sub-region, 433 or R3, a third PPG signal 403 is obtained. The respective segments S1, S2, S3, S4 and S5 of this PPG signal 403 are obtained respectively from the third quadrant pixels in the video frames 421 . . . 422 (excluding 422), 422 . . . 423 (excluding 423), 423 . . . 424 (excluding 424), 424 . . . 425 (excluding 425) and 425 . . . 426 (excluding 426). From the pixels of the fourth sub-region, 434 or R4, a fourth PPG signal 404 is obtained. The respective segments S1, S2, S3, S4 and S5 of this PPG signal 404 are obtained respectively from the fourth quadrant pixels in the video frames 421 . . . 422 (excluding 422), 422 . . . 423 (excluding 423), 423 . . . 424 (excluding 424), 424 . . . 425 (excluding 425) and 425 . . . 426 (excluding 426). In FIG. 4B, it is then assumed that a quality assessment is performed for the entire sub-region PPG signals 401, 402, 403 and 404. It is further assumed that the quality assessment reveals that sub-region PPG signals 401 and 402 are of bad quality, whereas sub-region PPG signals 403 and 404 are of good quality. Consequently, the sub-region PPG signals 403 and 404 are combined statically into multi-region PPG signal 405, e.g. through an averaged sum of these signals. The bad quality sub-region PPG signals 401 and 402 are removed and thus not used in the composition of the multi-region PPG signal 405. In the static multi-region PPG embodiment, illustrated by FIG. 4A and FIG. 4B, no individual segments of the sub-region signals are removed or selected for generation of the multi-region PPG signal 405. Although bad quality sub-region PPG signals 401 and 402 are removed, and good quality sub-region PPG signals 403 and 404 are maintained, it is still possible that bad quality segments that form part of the good quality PPG signals 403 and 404 are used in the multi-region PPG signal 405 and consequently negatively impact the accuracy of the multi-region PPG signal 405. It is also possible that good quality segments that form part of the bad quality PPG signals 401 and 402 are left unused, hence not exploiting all potential to compose an optimal multi-region PPG signal. The static multi-region PPG embodiment of the present invention, illustrated by FIG. 4A and FIG. 4B however is advantageous in that it requires limited processing to compose the multi-region PPG signal 405.

In a similar way, FIG. 5A shows video frames 521 . . . 522 . . . 523 . . . 524 . . . 525 . . . 526, taken at subsequent time moments by a lens similar to lens 301 in FIG. 3. Each video frame 521 is subdivided in four quadrants or sub-regions 531, 532, 533 and 534 respectively corresponding to sub-regions R1, R2, R3 and R4 of the lens. From the pixels of the first sub-region, 531 or R1, a first PPG signal 501 is obtained. The respective segments S1, S2, S3, S4 and S5 of this PPG signal 501 are obtained respectively from the first quadrant pixels in the video frames 521 . . . 522 (excluding 522), 522 . . . 523 (excluding 523), 523 . . . 524 (excluding 524), 524 . . . 525 (excluding 525) and 525 . . . 526 (excluding 526). From the pixels of the second sub-region, 532 or R2, a second PPG signal 502 is obtained. The respective segments S1, S2, S3, S4 and S5 of this PPG signal 502 are obtained respectively from the second quadrant pixels in the video frames 521 . . . 522 (excluding 522), 522 . . . 523 (excluding 523), 523 . . . 524 (excluding 524), 524 . . . 525 (excluding 525) and 525 . . . 526 (excluding 526). From the pixels of the third sub-region, 533 or R3, a third PPG signal 503 is obtained. The respective segments S1, S2, S3, S4 and S5 of this PPG signal 503 are obtained respectively from the third quadrant pixels in the video frames 521 . . . 522 (excluding 522), 522 . . . 523 (excluding 523), 523 . . . 524 (excluding 524), 524 . . . 525 (excluding 525) and 525 . . . 526 (excluding 526). From the pixels of the fourth sub-region, 534 or R4, a fourth PPG signal 504 is obtained. The respective segments S1, S2, S3, S4 and S5 of this PPG signal 504 are obtained respectively from the fourth quadrant pixels in the video frames 521 . . . 522 (excluding 522), 522 . . . 523 (excluding 523), 523 . . . 524 (excluding 524), 524 . . . 525 (excluding 525) and 525 . . . 526 (excluding 526). In FIG. 4B, it is then assumed that a quality assessment is performed for the individual segments S1, S2, S3, S4 and S5 of each of the sub-region PPG signals 501, 502, 503 and 504. It is further assumed that the quality assessment reveals that segments S1, S2, S3 and S4 of sub-region PPG signals 503 and 504 are of good quality, and segments S5 of sub-region signals PPG signals 501 and 502 are of good quality. All other segments are supposed to be of bad quality. Consequently, the good quality segments of the sub-region PPG signals 501, 502, 503 and 504 are dynamically combined to compose multi-region PPG signal 505. The segments S1 of sub-region PPG signals 503 and 504 are combined into segment S1 of multi-region PPG signal 505, e.g. through an averaged sum of these signals. Similarly, the segments S2 of sub-region PPG signals 503 and 504 are combined into segment S2 of multi-region PPG signal 505, the segments S3 of sub-region PPG signals 503 and 504 are combined into segment S3 of multi-region PPG signal 505, the segments S4 of sub-region PPG signals 503 and 504 are combined into segment S4 of multi-region PPG signal 505, and the segments S5 of sub-region PPG signals 501 and 502 are combined into segment S5 of multi-region PPG signal 505. The bad quality segments of sub-region PPG signals 501, 502, 503 and 504 are removed and thus not used in the composition of the multi-region PPG signal 505. The dynamic multi-region PPG embodiment illustrated by FIG. 5A and FIG. 5B is more processing intensive than the static multi-region PPG composition illustrated by FIG. 4A and FIG. 4B, but brings the advantage that all good quality segments of all sub-region PPG signals are used in order to generate a multi-region PPG signal 505 with enhanced accuracy and reliability. When compared with multi-region PPG signal 405, multi-region PPG signal 505 for instance contains the additional peak in segment S5, as a result of using the good quality segments S5 of PPG signals 501 and 502.

In a similar way, FIG. 6A shows video frames 621 . . . 622 . . . 623 . . . 624 . . . 625 . . . 626, taken at subsequent time moments by a lens similar to lens 301 in FIG. 3. Each video frame 621 is subdivided in four quadrants or sub-regions 631, 632, 633 and 634 respectively corresponding to sub-regions R1, R2, R3 and R4 of the lens, and for each of these quadrants 631, 632, 633 and 634 pixels of a first color C1 and pixels of a second color C2 are obtained. From the C1 pixels of the first sub-region, 631 or R1, a first PPG signal 601 is obtained and from the C2 pixels of the first sub-region, 631 or R1, a second PPG signal 602 is obtained. The respective segments S1, S2, S3, S4 and S5 of these PPG signals 601 and 602 are obtained respectively from the first quadrant C1 and C2 pixels in the video frames 621 . . . 622 (excluding 622), 622 . . . 623 (excluding 623), 623 . . . 624 (excluding 624), 624 . . . 625 (excluding 625) and 625 . . . 626 (excluding 626). From the C1 pixels of the second sub-region, 632 or R2, a third PPG signal 603 is obtained. From the C2 pixels of the second sub-region, 632 or R2, a fourth PPG signal 604 is obtained. The respective segments S1, S2, S3, S4 and S5 of these PPG signals 603 and 604 are obtained respectively from the second quadrant C1 and C2 pixels in the video frames 621 . . . 622 (excluding 622), 622 . . . 623 (excluding 623), 623 . . . 624 (excluding 624), 624 . . . 625 (excluding 625) and 625 . . . 626 (excluding 626). From the C1 pixels of the third sub-region, 633 or R3, a fifth PPG signal 605 is obtained. From the C2 pixels of the third sub-region, 633 or R3, a sixth PPG signal 606 is obtained. The respective segments S1, S2, S3, S4 and S5 of these PPG signals 605 and 606 are obtained respectively from the third quadrant C1 and C2 pixels in the video frames 621 . . . 622 (excluding 622), 622 . . . 623 (excluding 623), 623 . . . 624 (excluding 624), 624 . . . 625 (excluding 625) and 625 . . . 626 (excluding 626). From the C1 pixels of the fourth sub-region, 634 or R4, a seventh PPG signal 607 is obtained. From the C2 pixels of the fourth sub-region, 634 or R4, an eight PPG signal 608 is obtained. The respective segments S1, S2, S3, S4 and S5 of these PPG signals 607 and 608 are obtained respectively from the fourth quadrant C1 and C2 pixels in the video frames 621 . . . 622 (excluding 622), 622 . . . 623 (excluding 623), 623 . . . 624 (excluding 624), 624 . . . 625 (excluding 625) and 625 . . . 626 (excluding 626). In FIG. 6B, it is then assumed that a quality assessment is performed for the individual segments S1, S2, S3, S4 and S5 of each of the sub-region PPG signals

601-608. It is further assumed that for the first color C1, the quality assessment reveals that segments S1, S2, S3 and S4 of sub-region PPG signals 605 and 607 are of good quality, and segments S5 of sub-region signals PPG signals 601 and 603 are of good quality. All other segments in the C1 PPG signals 601, 603, 605 and 607 are supposed to be of bad quality. Consequently, the good quality C1 segments of the sub-region PPG signals 601, 603, 605 and 607 are dynamically combined to compose a multi-region PPG signal 609 for the first color C1. The segments S1 of sub-region PPG signals 605 and 607 are combined into segment S1 of multi-region PPG signal 609, e.g. through an averaged sum of these signals. Similarly, the segments S2 of sub-region PPG signals 605 and 607 are combined into segment S2 of multi-region PPG signal 609, the segments S3 of sub-region PPG signals 605 and 607 are combined into segment S3 of multi-region PPG signal 609, the segments S4 of sub-region PPG signals 605 and 607 are combined into segment S4 of multi-region PPG signal 609, and the segments S5 of sub-region PPG signals 601 and 603 are combined into segment S5 of multi-region PPG signal 609. The bad quality segments of sub-region PPG signals 601, 603, 605 and 607 are removed and thus not used in the composition of the multi-region PPG signal 609 for the first color C1. It is further assumed that for the second color C2, the quality assessment reveals that segments S1, S2 and S3 of sub-region PPG signals 602 and 604 are of good quality, and segments S4 and S5 of sub-region signals PPG signals 604, 606 and 608 are of good quality. All other segments in the C2 PPG signals 602, 604, 606 and 608 are supposed to be of bad quality. Consequently, the good quality C2 segments of the sub-region PPG signals 602, 604, 606 and 608 are dynamically combined to compose a multi-region PPG signal 610 for the second color C2. The segments S1 of sub-region PPG signals 602 and 604 are combined into segment S1 of multi-region PPG signal 610, e.g. through an averaged sum of these signals. Similarly, the segments S2 of sub-region PPG signals 602 and 604 are combined into segment S2 of multi-region PPG signal 610, the segments S3 of sub-region PPG signals 602 and 604 are combined into segment S3 of multi-region PPG signal 610, the segments S4 of sub-region PPG signals 604, 606 and 608 are combined into segment S4 of multi-region PPG signal 610, and the segments S5 of sub-region PPG signals 604, 606 and 608 are combined into segment S5 of multi-region PPG signal 610. The bad quality segments of sub-region PPG signals 602, 604, 606 and 608 are removed and thus not used in the composition of the multi-region PPG signal 610 for the second color C2. Thereafter, a quality assessment is made for the multi-region PPG signals 609 and 610 in order to select the best color, i.e. the color whose multi-region PPG signal has the best quality score according to some quality measure. In FIG. 6B, it is assumed that the quality assessment reveals that multi-region PPG signal 609 has a better quality than multi-region PPG signal 610. As a result, the first color C1 is selected. The dynamic multi-region PPG embodiment with color selection illustrated by FIG. 6A and FIG. 6B is even more processing intensive, but brings the advantage that all good quality segments of all sub-region PPG signals are used and this for plural colors. Furthermore, the best color is selected in order to optimize the accuracy and reliability of the multi-region PPG signal without requiring the different colors to be synchronized.

In a similar way, FIG. 7A shows video frames 721 . . . 722 . . . 723 . . . 724 . . . 725 . . . 726, taken at subsequent time moments by a lens similar to lens 301 in FIG. 3. Each video frame 721 is subdivided in four quadrants or sub-regions 731, 732, 733 and 734 respectively corresponding to sub-regions R1, R2, R3 and R4 of the lens, and for each of these quadrants 731, 732, 733 and 734 pixels of a first color C1 and pixels of a second color C2 are obtained. From the C1 pixels of the first sub-region, 731 or R1, a first PPG signal 701 is obtained and from the C2 pixels of the first sub-region, 731 or R1, a second PPG signal 702 is obtained. The respective segments S1, S2, S3, S4 and S5 of these PPG signals 701 and 702 are obtained respectively from the first quadrant C1 and C2 pixels in the video frames 721 . . . 722 (excluding 722), 722 . . . 723 (excluding 723), 723 . . . 724 (excluding 724), 724 . . . 725 (excluding 725) and 725 . . . 726 (excluding 726). From the C1 pixels of the second sub-region, 732 or R2, a third PPG signal 703 is obtained. From the C2 pixels of the second sub-region, 732 or R2, a fourth PPG signal 704 is obtained. The respective segments S1, S2, S3, S4 and S5 of these PPG signals 703 and 704 are obtained respectively from the second quadrant C1 and C2 pixels in the video frames 721 . . . 722 (excluding 722), 722 . . . 723 (excluding 723), 723 . . . 724 (excluding 724), 724 . . . 725 (excluding 725) and 725 . . . 726 (excluding 726). From the C1 pixels of the third sub-region, 733 or R3, a fifth PPG signal 705 is obtained. From the C2 pixels of the third sub-region, 733 or R3, a sixth PPG signal 706 is obtained. The respective segments S1, S2, S3, S4 and S5 of these PPG signals 705 and 706 are obtained respectively from the third quadrant C1 and C2 pixels in the video frames 721 . . . 722 (excluding 722), 722 . . . 723 (excluding 723), 723 . . . 724 (excluding 724), 724 . . . 725 (excluding 725) and 725 . . . 726 (excluding 726). From the C1 pixels of the fourth sub-region, 734 or R4, a seventh PPG signal 707 is obtained. From the C2 pixels of the fourth sub-region, 734 or R4, an eight PPG signal 708 is obtained. The respective segments S1, S2, S3, S4 and S5 of these PPG signals 707 and 708 are obtained respectively from the fourth quadrant C1 and C2 pixels in the video frames 721 . . . 722 (excluding 722), 722 . . . 723 (excluding 723), 723 . . . 724 (excluding 724), 724 . . . 725 (excluding 725) and 725 . . . 726 (excluding 726). In FIG. 7B, it is then assumed that a quality assessment is performed for the individual segments S1, S2, S3, S4 and S5 of each of the sub-region PPG signals 701-708. It is further assumed that for the first color C1, the quality assessment reveals that segments S1, S2, S3 and S4 of sub-region PPG signals 705 and 707 are of good quality, and segments S5 of sub-region signals PPG signals 701 and 703 are of good quality. All other segments in the C1 PPG signals 701, 703, 705 and 707 are supposed to be of bad quality. It is further assumed that for the second color C2, the quality assessment reveals that segments S1, S2 and S3 of sub-region PPG signals 702 and 704 are of good quality, and segments S4 and S5 of sub-region signals PPG signals 704, 706 and 708 are of good quality. All other segments in the C2 PPG signals 702, 704, 706 and 708 are supposed to be of bad quality. The good quality segments of plural colors that are temporarily corresponding and that are supposed to be synchronised are then dynamically combined into a single multi-color multi-region PPG signal 709. Thus, the segments S1 of sub-region PPG signals 702, 704, 705 and 707 are combined into segment S1 of multi-region PPG signal 709, e.g. through an averaged sum of these signals. Similarly, the segments S2 of sub-region PPG signals 702, 704, 705 and 707 are combined into segment S2 of multi-region PPG signal 709, the segments S3 of sub-region PPG signals 702, 704, 705 and 707 are combined into segment S3 of multi-region PPG signal 709, the segments S4 of sub-region PPG signals 704, 705, 706, 707 and 708 are combined into segment S4 of multi-region PPG signal 709, and the segments S5 of sub-region PPG signals 701, 703, 704, 706 and 708 are combined into segment S5 of multi-region PPG signal 709. The bad quality segments of sub-region PPG signals 701-708 are removed and thus not used in the composition of the multi-region PPG signal 709. The dynamic multi-color multi-region PPG embodiment illustrated by FIG. 7A and FIG. 7B is even more processing intensive and requires synchronization between the colors C1 and C2, but it brings the advantage that all good quality segments of all sub-region PPG signals and all colors are combined. This way, a PPG signal 709 is composed with optimal accuracy and reliability. Compared with the embodiment illustrated by FIG. 6A and FIG. 6B, it is noticed for instance that the multi-color multi-region PPG signal 709 obtained through dynamic combination of regions and colors also contains the peak in segment S4, whereas this peak remains absent in the multi-region PPG signal 609 obtained through dynamic combination of regions with color selection.

FIG. 8 illustrates a possible implementation of the peak detection step 106 in FIG. 1. In the multi-region PPG signal 801, peaks are detected, e.g. by comparing the signal strength with the average signal strength. Detected peaks in multi-region PPG signal 801 are marked with a dot. These peaks are then windowed and the windowed peaks are averaged to generate a peak template 802, i.e. a model peak. Thereafter, each detected peak is correlated with the peak template 802. Peaks for which the correlation exceeds a certain correlation threshold are maintained. Peaks for which the correlation stays below the correlation threshold, like for instance 803 in FIG. 8, are removed. With the remaining peaks, the steps of averaging to generate a peak template, correlating to identify peaks that are kept and peaks that are dropped, are iteratively repeated until a stable situation is reached wherein no peaks are dropped anymore.

Figure 9:
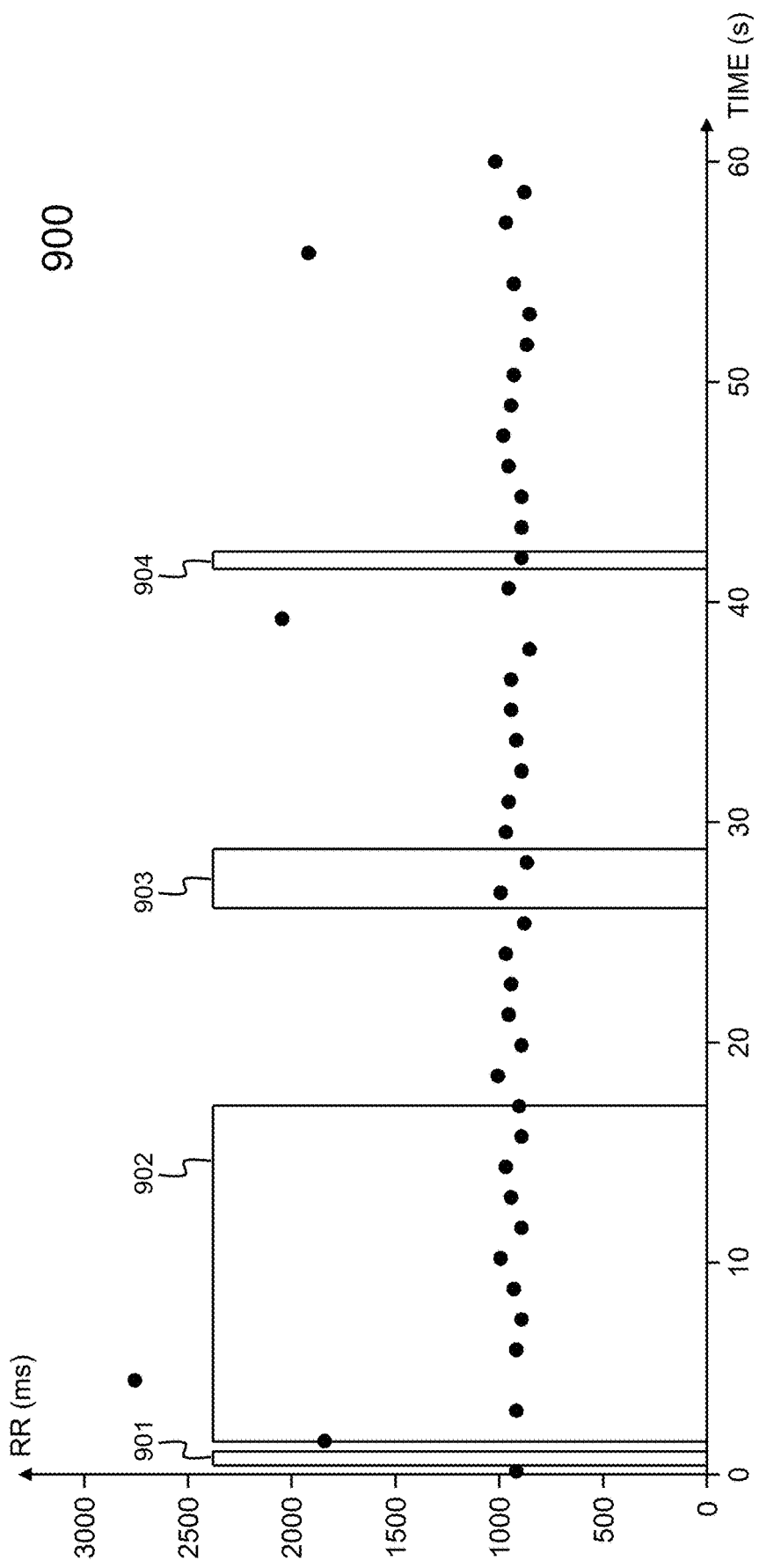
FIG. 9 illustrates the step of RR-tachogram extraction in embodiments of the computer-implemented method for contact PPG according to the present invention.

FIG. 9 illustrates a possible implementation of the RR-tachogram extraction step 107 in FIG. 1. The RR-tachogram 900 has the time as horizontal axis and the time difference between subsequent peaks in the multi-region PPG signal as vertical axis. Hence, the RR-tachogram shows the variability in the peak rate, i.e. the variability in the heartrate in case the peaks in the multi-region PPG signal represent heart pulses of a monitored person. The reliability of the extracted RR-tachogram may be improved by performing a quality analysis of the multi-region PPG signal. This quality analysis may be done using a quality assessment technique similar to the one described here above, i.e. based on wavelet transforming and neural network analysis, but the skilled person will appreciate that other quality analysis techniques may applied as well to identify good quality portions and bad quality portions in the multi-region PPG signal. RR-intervals that are located entirely or partially within a bad quality portion of the multi-region PPG signal, like 901, 902, 903 and 904 in FIG. 9. This way, a processed, more reliable RR-tachogram is obtained. From the RR-tachogram, the variability in the peak rate can be determined. If this variability exceeds certain thresholds, corresponding atrial fibrillation risk score values may be reported to the monitored person or his physician.

Figure 10:
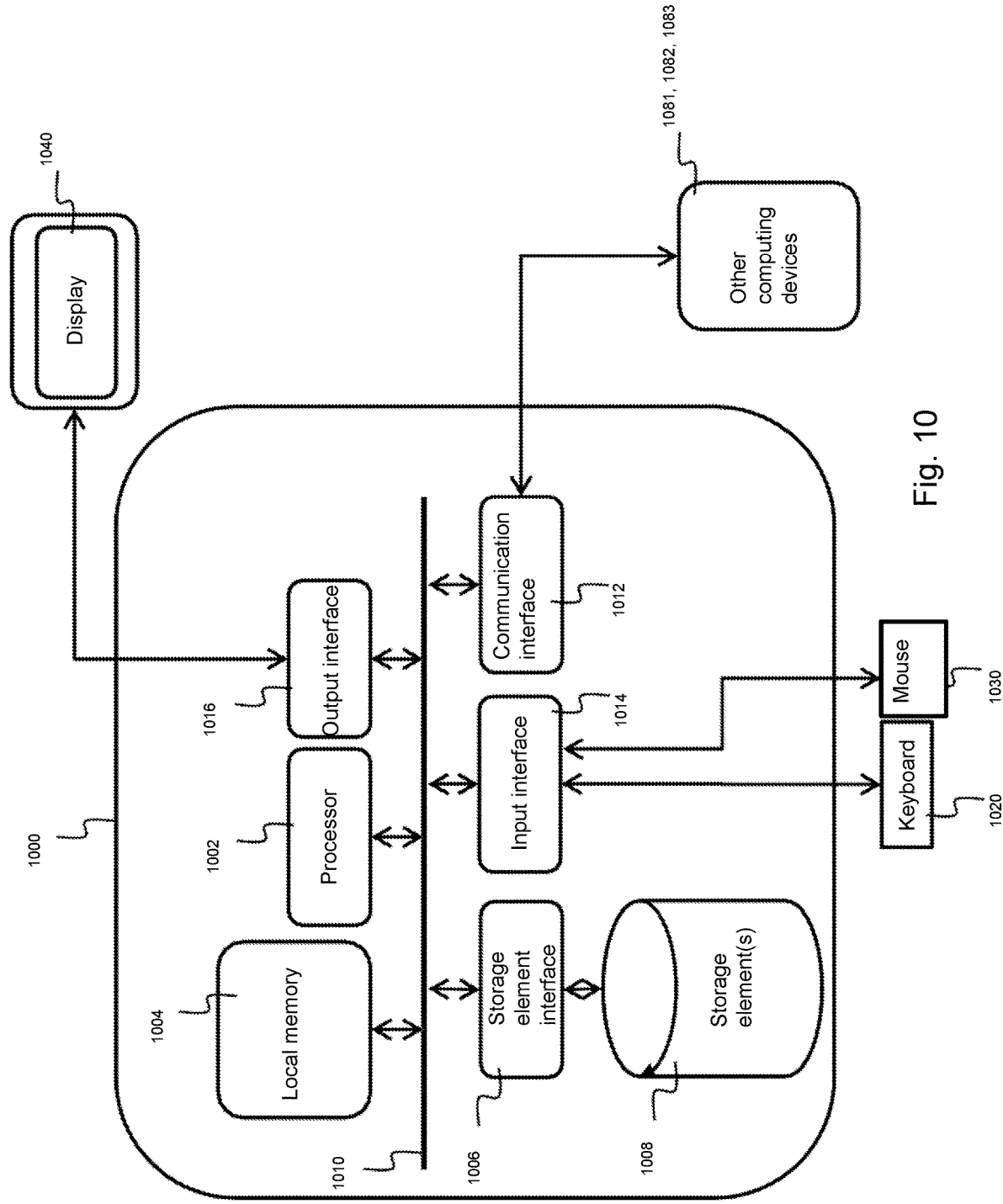
FIG. 10 illustrates a suitable computing system 1000 for realizing methods and devices according to embodiments of the invention.

FIG. 10 shows a suitable computing system 1000 according to an embodiment of the invention. Computing system 1000 is suitable for implementing embodiments of the method for contact PPG in according with the present invention. Computing system 1000 may in general be formed as a suitable general-purpose computer and comprise a bus 1010, a processor 1002, a local memory 1004, one or more optional input interfaces 1014, one or more optional output interfaces 1016, a communication interface 1012, a storage element interface 1006 and one or more storage elements 1008. Bus 1010 may comprise one or more conductors that permit communication among the components of the computing system 1000. Processor 1002 may include any type of conventional processor or microprocessor that interprets and executes programming instructions. Local memory 1004 may include a random access memory (RAM) or another type of dynamic storage device that stores information and instructions for execution by processor 1002 and/or a read only memory (ROM) or another type of static storage device that stores static information and instructions for use by processor 1002. Input interface 1014 may comprise one or more conventional mechanisms that permit an operator or user to input information to the computing device 1000, such as a keyboard 1020, a mouse 1030, a pen, voice recognition and/or biometric mechanisms, a camera, etc. Output interface 1016 may comprise one or more conventional mechanisms that output information to the operator or user, such as a display 1040, etc. Communication interface 1012 may comprise any transceiver-like mechanism such as for example one or more Ethernet interfaces that enables computing system 1000 to communicate with other devices and/or systems, for example with other computing devices 1081, 1082, 1083. The communication interface 1012 of computing system 1000 may be connected to such another computing system by means of a local area network (LAN) or a wide area network (WAN) such as for example the internet. Storage element interface 1006 may comprise a storage interface such as for example a Serial Advanced Technology Attachment (SATA) interface or a Small Computer System Interface (SCSI) for connecting bus 1010 to one or more storage elements 1008, such as one or more local disks, for example SATA disk drives, and control the reading and writing of data to and/or from these storage elements 1008. Although the storage elements 1008 above is described as a local disk, in general any other suitable computer-readable media such as a removable magnetic disk, optical storage media such as a CD or DVD, -ROM disk, solid state drives, flash memory cards, . . . could be used. It is noticed that the entire method according to the present invention can be executed centralized, e.g. on a server in a management centre or in a cloud system, or it can be partially executed on a remote electronic device, e.g. worn by the user, and partially on a central server. Computing system 1000 could thus correspond to the processing system available centrally or the processing system available in the electronic device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A computer-implemented method for contact photoplethysmography, abbreviated contact PPG, comprising:
    obtaining during a time interval plural PPG signals for respective sub-regions of a lens or video frame, each sub-region of said sub-regions covering multiple pixels;
    assessing a quality of said PPG signals or portions thereof and detecting inversion of said PPG signals or portions thereof;
    reverting said PPG signals or portions of said PPG signals that are inverted;
    removing bad quality segments from said PPG signals; and
    combining good quality PPG signals or temporally corresponding good quality segments of said plural PPG signals, comprising non-inverted and reverted inverted PPG signals or segments, to thereby obtain a multi-region PPG signal.

2. The computer-implemented method for contact PPG according to claim 1, further comprising:
    processing each PPG signal of said plural PPG signals to identify said good quality segments of said PPG signal wherein a quality measure of said PPG signal is above a threshold and said bad quality segments of said PPG signal wherein said quality measure of said PPG signal is below said threshold.

3. The computer-implemented method for contact PPG according to claim 1, further comprising:
    processing each PPG signal, said processing comprising:
    wavelet transforming said PPG signal to obtain a wavelet transformed PPG signal; and
    supplying said wavelet transformed PPG signal to a neural network trained to identify said good quality segments of said PPG signal and said bad quality segments of said PPG signal.

4. The computer-implemented method for contact PPG according to claim 1, wherein a neural network is further trained to identify said inverted segments.

5. The computer-implemented method for contact PPG according to claim 1, comprising:
    generating plural multi-region PPG signals similar to said multi-region PPG signal for respective colors from a color space.

6. The computer-implemented method for contact PPG according to claim 5, further comprising:
    determining a quality measure for each one of said colors; and
    selecting amongst said plural multi-region PPG signals the multi-region PPG signal for the color with highest quality measure.

7. The computer-implemented method for contact PPG according to claim 6, further comprising:
    determining a quality measure for each one of said colors; and
    combining multi-region PPG signals for plural colors into a multi-color multi-region PPG signal.

8. The computer-implemented method for contact PPG according to claim 7, further comprising:
    obtaining during said time interval plural PPG signals for respective colors and respective sub-regions;
    processing each PPG signal of said plural PPG signals to identify good quality segments of said PPG signal wherein a quality measure of said PPG signal is above a threshold and bad quality segments of said PPG signal wherein said quality measure of said PPG signal is below said threshold;
    removing said bad quality segments from each PPG signal of said plural PPG signals; and
    combining temporal corresponding good quality segments of said plural PPG signals to obtain said multi-color multi-region PPG signal.

9. The computer-implemented method for contact PPG according to claim 1, further comprising locking settings of said lens during said time interval, said settings at least comprising:
    diaphragm; and
    light sensitivity or light exposure.

10. The computer-implemented method for contact PPG according to claim 1, further comprising detecting peaks in said multi-region PPG signal, and thereto:
    detecting initial peaks in said multi-region PPG signal;
    windowing said initial peaks in said multi-region PPG signal to thereby generate windowed initial peaks;
    averaging said windowed initial peaks in said multi-region PPG signal to thereby generate a peak template;
    correlating said initial peaks with said peak template;
    maintaining initial peaks for which a correlation measure exceeds a correlation threshold as peaks; and
    dropping initial peaks for which said correlation measure does not exceed said correlation threshold.

11. The computer-implemented method for contact PPG according to claim 10, further comprising:
    extracting an RR-tachogram by determining a time difference between subsequent peaks in said multi-region PPG signal.

12. The computer-implemented method for contact PPG according to claim 11, further comprising:
    processing said multi-region PPG signal to identify good quality segments of said multi-region PPG signal wherein a quality measure of said multi-region PPG signal is above a threshold and bad quality segments of said multi-region PPG signal wherein said quality measure of said multi-region PPG signal is below said threshold;
    removing peaks within said bad quality segments from said multi-region PPG signal before extracting said RR-tachogram; and
    removing from said RR-tachogram intervals located totally or partially within said bad quality segments of said multi-region PPG signal.

13. The computer-implemented method for contact PPG according to claim 11, further comprising:
    determining a variability in said time difference between subsequent peaks; and determining from said variability an atrial fibrillation risk score.

14. A non-transitory computer readable storage medium comprising a computer program product comprising computer-executable instructions for performing the method according to claim 1 when the program is run on a computer.

15. A data processing system programmed for carrying out the method according to claim 1.

16. A computer-implemented method for contact photoplethysmography, abbreviated contact PPG, comprising:
   obtaining during a time interval plural PPG signals for respective sub-regions of a lens or video frame, each sub-region of said sub-regions covering multiple pixels;
   combining said plural PPG signals to thereby obtain a multi-region PPG signal; and
   generating plural multi-region PPG signals similar to said multi-region PPG signal for respective colors from a color space.

17. A computer-implemented method for contact photoplethysmography, abbreviated contact PPG, comprising:
   obtaining during a time interval plural PPG signals for respective sub-regions of a lens or video frame, each sub-region of said sub-regions covering multiple pixels;
   combining said plural PPG signals to thereby obtain a multi-region PPG signal; and
   detecting peaks in said multi-region PPG signal, and thereto:
      detecting initial peaks in said multi-region PPG signal;
      windowing said initial peaks in said multi-region PPG signal to thereby generate windowed initial peaks;
      averaging said windowed initial peaks in said multi-region PPG signal to thereby generate a peak template;
      correlating said initial peaks with said peak template;
      maintaining initial peaks for which a correlation measure exceeds a correlation threshold as peaks; and
      dropping initial peaks for which said correlation measure does not exceed said correlation threshold.

* * * * *